United States Patent
Chiu et al.

[11] Patent Number: 5,870,203
[45] Date of Patent: Feb. 9, 1999

[54] ADAPTIVE LIGHTING CONTROL APPARATUS FOR ILLUMINATING A VARIABLE-SPEED WEB FOR INSPECTION

[75] Inventors: Chinchuan Chiu, New City, N.Y.; Wing Loom Chek, Singapore, Singapore; Philip Paolella, Waldwick, N.J.

[73] Assignees: Sony Corporation, Tokyo, Japan; Sony Electronics, Inc, Park Ridge, N.J.

[21] Appl. No.: 616,377
[22] Filed: Mar. 15, 1996
[51] Int. Cl.⁶ ................................ G01N 21/89
[52] U.S. Cl. ..................... 356/430; 250/559.46
[58] Field of Search ............. 356/430, 23; 250/559.45, 250/559.46

[56] References Cited

U.S. PATENT DOCUMENTS

| | | |
|---|---|---|
| 3,761,177 | 9/1973 | Corse ........................... 356/23 |
| 4,377,746 | 3/1983 | Kopineck et al. ............ 356/430 X |
| 4,641,256 | 2/1987 | Marchegiano ................ 356/430 X |
| 4,930,889 | 6/1990 | Van Donselaar et al. ..... 356/430 X |

*Primary Examiner*—Vincent P. McGraw
*Attorney, Agent, or Firm*—Frommer Lawrence & Haug LLP; William S. Frommer

[57] ABSTRACT

A lighting control apparatus for illuminating a moving variable-speed web for inspection with a camera is provided. The apparatus is comprised of a detecting device for detecting the positioning of the web; a lighting device, aligned with the camera, for emitting a light to illuminate the web; a calculating device for calculating the speed of the web; and a control device which controls the emission of light by the lighting device as a function of the speed of the web.

16 Claims, 11 Drawing Sheets

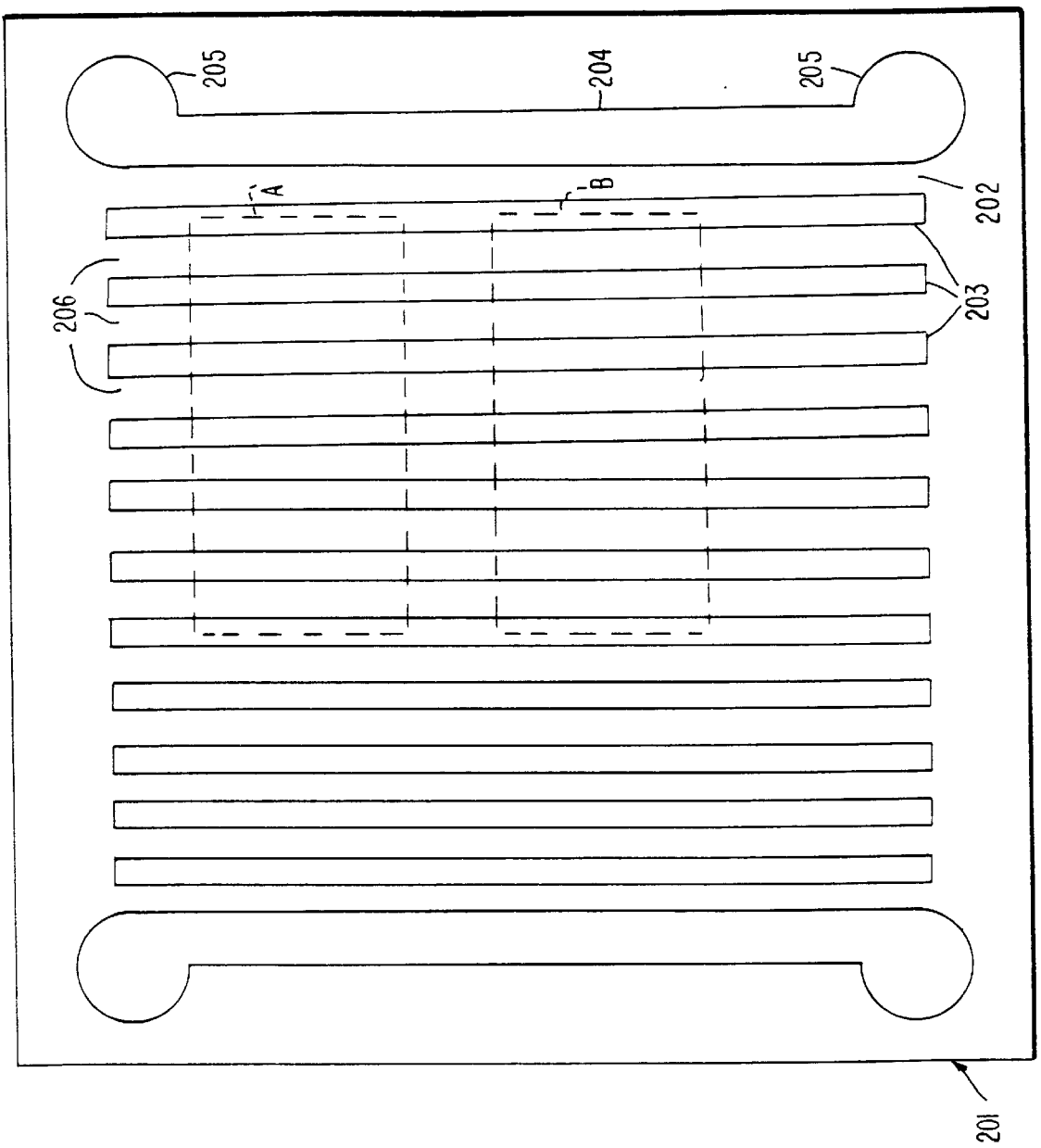

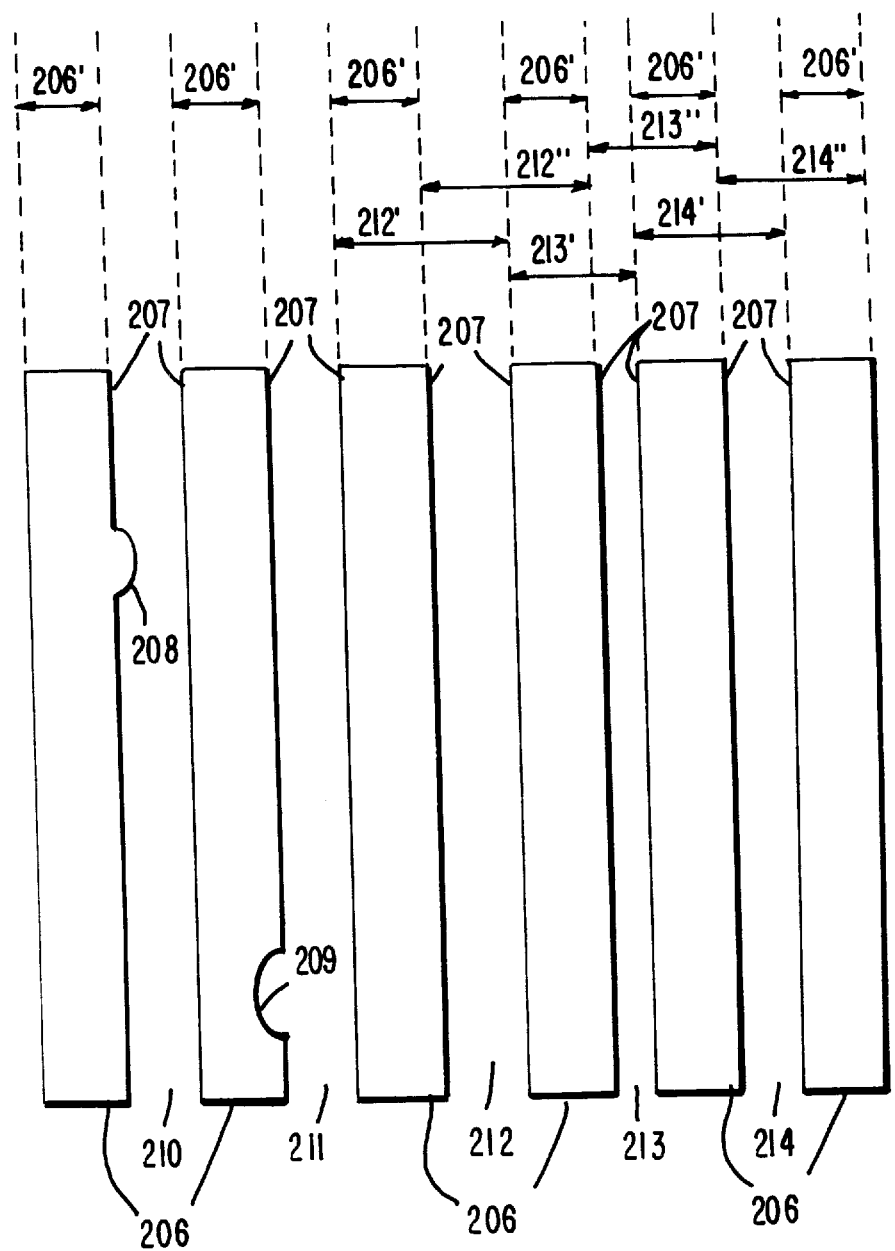

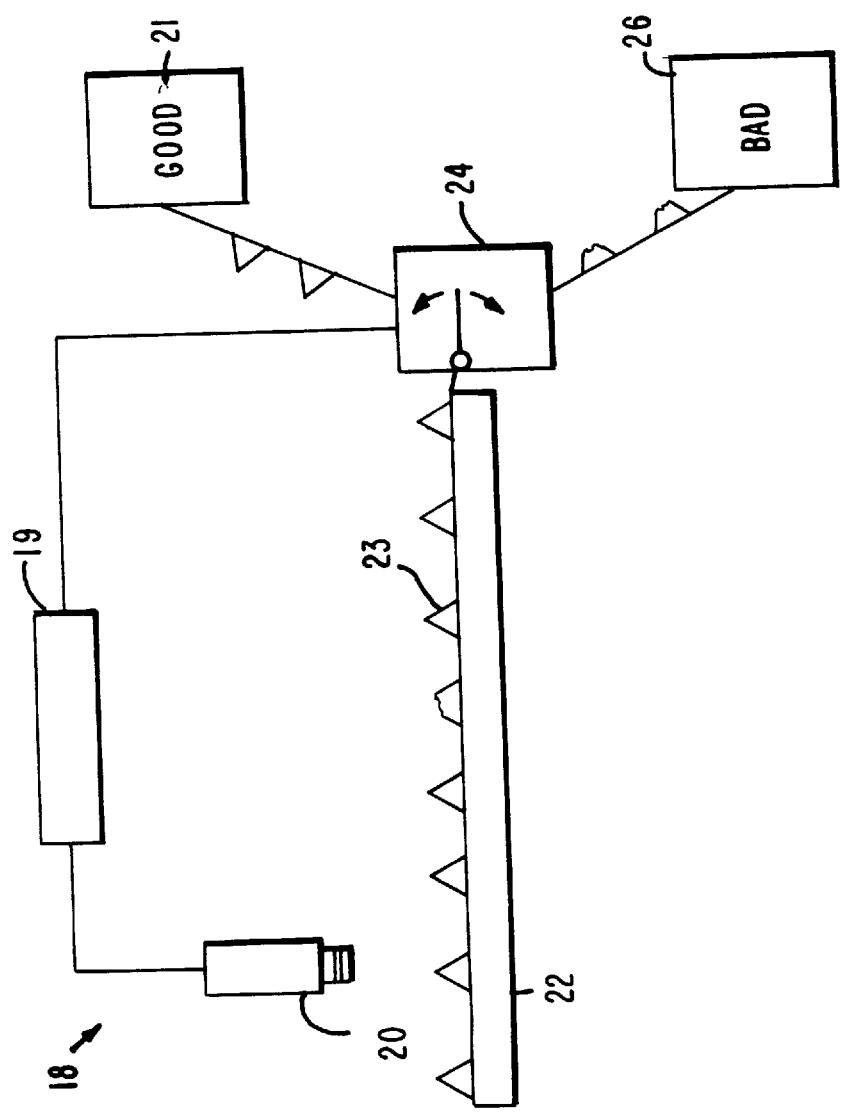

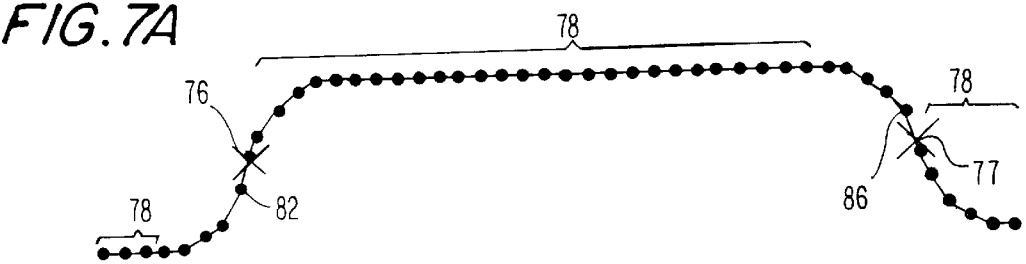
FIG. 7A
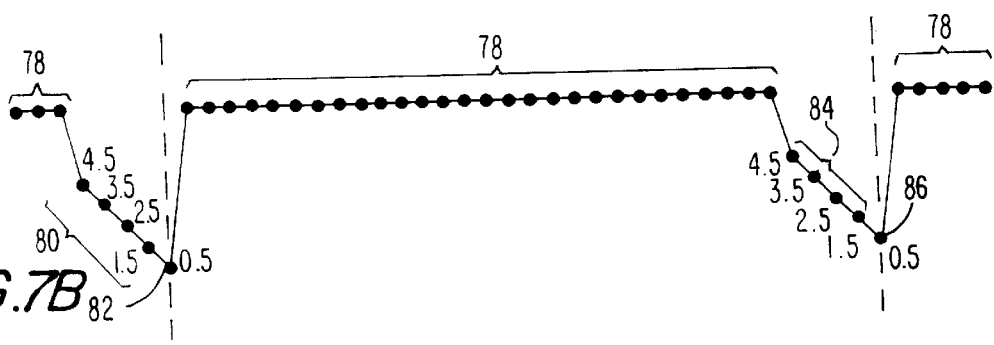
FIG. 7B
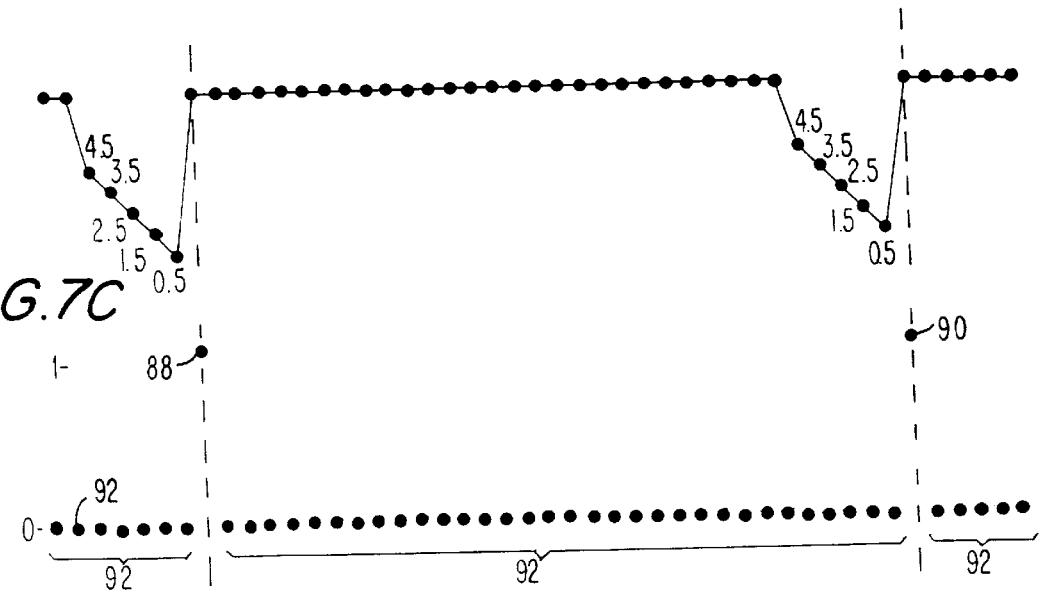
FIG. 7C
FIG. 7D

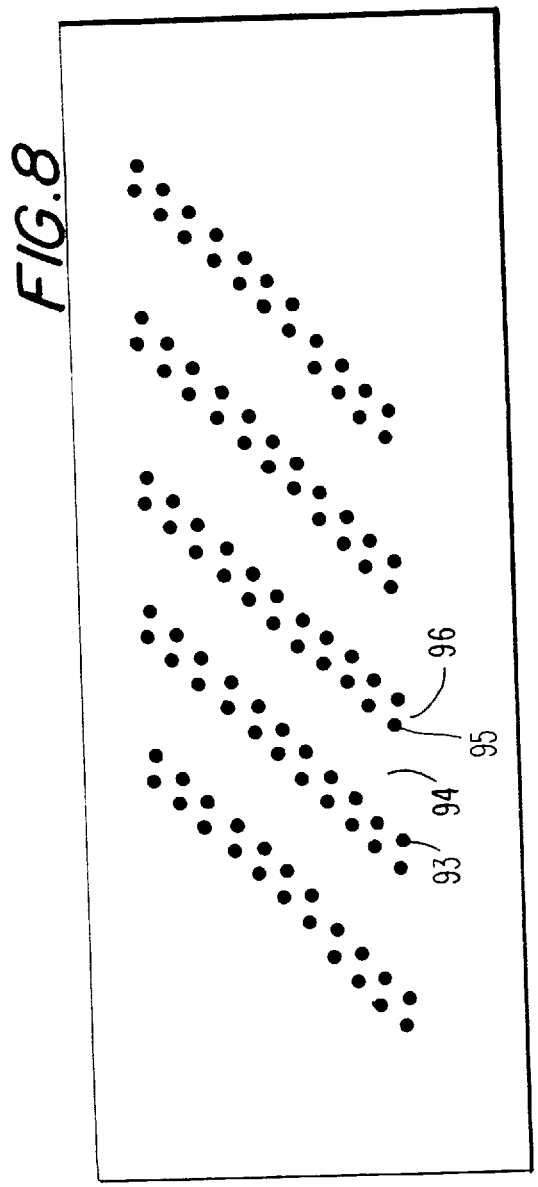

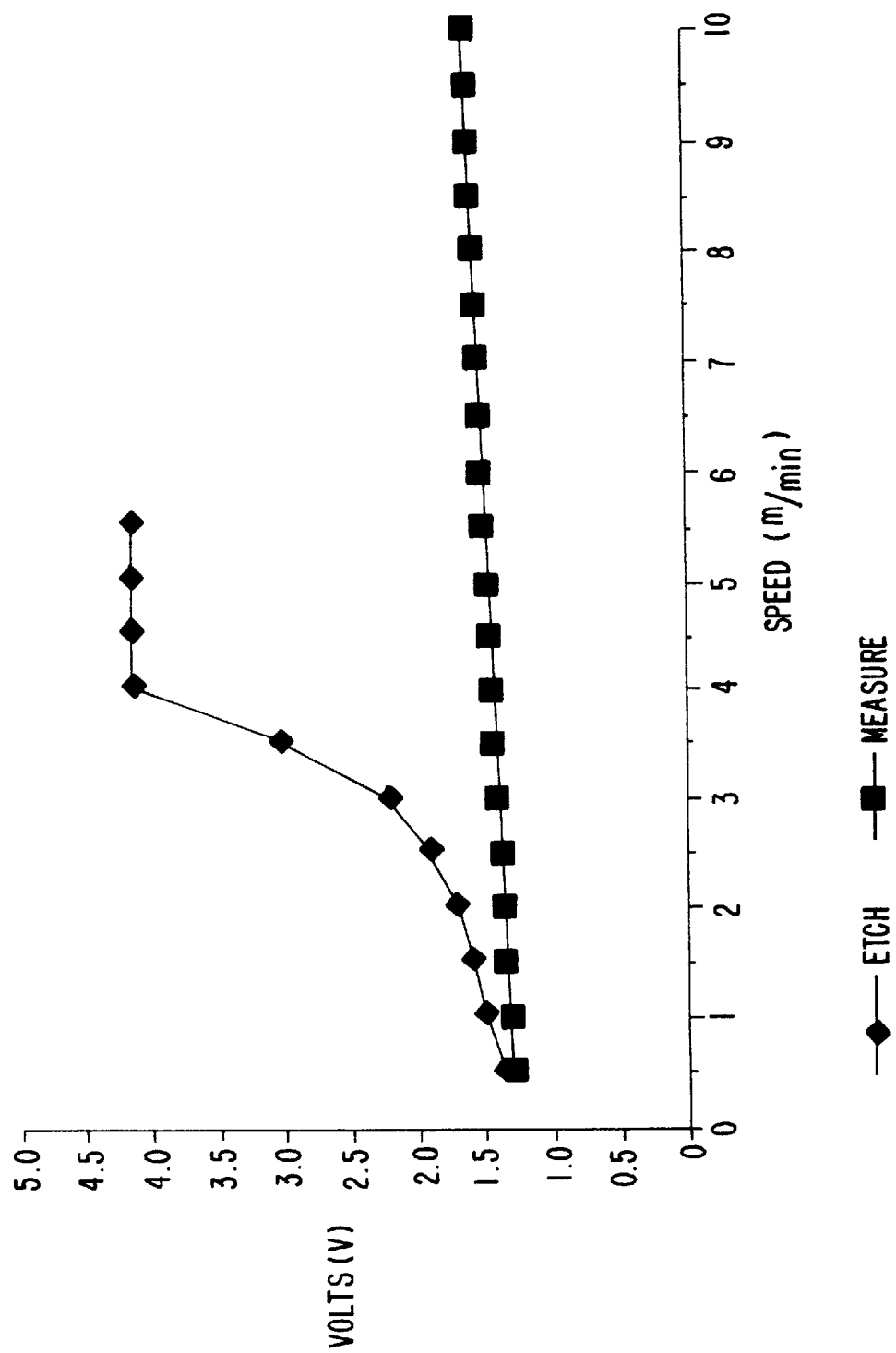

ADAPTIVE LIGHTING CONTROL APPARATUS FOR ILLUMINATING A VARIABLE-SPEED WEB FOR INSPECTION

BACKGROUND OF THE INVENTION

This invention relates to adaptive lighting control apparatus for illuminating a variable-speed web for visual inspection and measurement of the features of segments of the web and, more particularly, to such apparatus for illuminating a perforated segment of the web to allow detection of etch defects and measurement of the dimensions of such defects.

Despite efforts to insure uniformity, modern manufacturing processes continue to mass-produce products with varying characteristics. Inspection mechanisms are utilized to sort units of product according to the individual characteristics of each. In some applications, both objective and subjective quality standards are applied to judge a product's characteristics. Extremely fine gradations of quality can pose a difficult inspection challenge.

In some industries, teams of human inspectors are employed to inspect the output of mass-production manufacturing to determine the compliance of each unit of product with the applicable standards. Relative to automated manufacturing, the process of human inspection has proven to be slow, inefficient, and costly, thereby limiting overall manufacturing throughput. In some industrial settings human inspection is entirely infeasible because the demands for speed and accuracy simply exceed human capacity.

At present, human inspectors are still utilized by video display manufacturers to inspect video display components. A particularly time-consuming and exhausting task is the inspection of aperture grills. An example of an aperture grill 201 is illustrated in FIGS. 1A, 1B and 1C. An aperture grill is used during the manufacture of video displays to mask the interior surface of a display screen for the application of phosphorus coatings. Also, aperture grills are physically incorporated into video display screens as a means for focusing an incident beam of electrons from an electron gun.

Typically, an aperture grill 201 is comprised of a thin sheet 202 of material, preferably metal, in which a number of openings 203 and 204 have been formed. As depicted in FIG. 1A, the aperture grill 201 includes a number of openings 203, preferably substantially rectangular. Long, thin and substantially rectangular openings are referred to as "slits". The long, thin portions of the sheet 202 that remain interspersed among the openings 203 are called "ribbons" 206, also referred to as "tapes". In the following discussion, the terms "slits" and "ribbons" should be understood to include "openings" and "tapes", respectively.

In a preferred embodiment, the width of each of slits 203 is between 140 and 260 microns and the width of each of ribbons 206 is between 500 and 1000 microns. These ranges are given merely as examples, as an aperture grill need not be so limited At each end of the aperture grill 201 and substantially parallel to the slits 203, is a breakaway tab 204. Each breakaway tab 204 preferably consists of an opening with two long straight sides and two curved ends 205. An aperture grill may be perforated with a number of additional openings; however, description of such has been omitted in the interest of brevity.

FIG. 1B presents a magnified illustration of area A of FIG. 1A. FIG. 1B illustrates ribbons 206, ribbon widths 206', pairs of edges 207, under-etch defect 208, over-etch defect 209, slits 210–214, pitches 212'–214', and pitches 212"–214". It will be understood that the dotted portions of FIG. 1B represent extensions of each of ribbons 206.

Under-etch defect 208 and over-etch defect 209 result from process variations which occur during the etching of the slits 210–214. As illustrated, under-etch defect 208 results in an excess of material protruding from one of ribbons 206 into a slit 210. Consequently, the under-etch defect 208 interrupts one of the otherwise substantially straight edges 207 of slit 210. Similarly, over-etch defect 209 results in a localized void in one of ribbons 206, increasing the width of a slit 211 at that location. Consequently, the over-etch defect 209 interrupts one of the otherwise substantially straight edges 207 of slit 211.

An etch defect of large enough size will render a particular aperture grill unsuitable for use. Specifically, an aperture grill containing a single etch defect having dimensions greater than 50 microns by 150 microns will cause an undesirable blemish on an operating video display into which it is incorporated. However, the detection of even smaller defects may be necessary and the present invention is not limited to the detection of defects of any particular dimensions.

In FIG. 1B, the slits 210, 211, and 214 have approximately the same width (ignoring localized defects), whereas slit 212 is relatively wider and slit 213 is relatively thinner. Each of ribbons 206 has the same width (ribbon width 206').

A "pitch" may be defined as the distance between two corresponding edges of two adjacent pairs of edges 207 (e.g. the distance between the left-hand edges or the right-hand edges of two adjacent slits). Thus, there are at least two ways to define the pitches of an aperture grill. For example, pitch 212' is the distance between the right-hand edge of slit 211 and the right-hand edge of slit 212, and thus spans slit 212. Pitch 212" is the distance between the left-hand edge of slit 212 and the left-hand edge of slit 213.

As illustrated in FIG. 1B, it is apparent that the pitch (212', 212") spanning slit 212 is greater than the pitch (214', 214") spanning slit 214. In contrast, the pitch spanning slit 213 (213', 213") is less than the pitch spanning slit 214 (214', 214"). A pitch defect is defined as a pitch which varies substantially from the average of the pitches of an aperture grill. For a typical video display, pitch defects in excess of three percent of the average pitch of the aperture grill are noticeable to the human eye, and render the aperture grill unsuitable for use. Pitches 212' (212") and 213' (213") illustrate two types of pitch defects.

Another type of defect that occurs in aperture grills is a width defect. Examples of four width defects are provided in FIG. 1C. FIG. 1C presents a magnified illustration of area B of FIG. 1A. FIG. 1C illustrates ribbons 206, 206a, and 206b; ribbon widths 206', 206a', and 206b'; slits 215–217; and slit widths 215'–217'. As depicted, each of ribbons 206 is of the same width 206', whereas ribbon 206a has a greater width 206a' and ribbon 206b has a lesser width 206b'. Each of slits 215 is of the same width 215', whereas slit 216 has a lesser width 216' and slit 217 has a greater width 217'.

If it is assumed that width 206' is a typical ribbon width and width 215' is a typical slit width, then ribbon 206a demonstrates a first type of width defect as it is wider than ribbon 206, i.e. 206a' is greater than 206'. Ribbon 206b demonstrates a second type of width defect as it is thinner than ribbon 206, i.e. 206b' is less than 206'. Slit 216 demonstrates a third type of width defect as it is thinner than slit 215, i.e. 216' is less than 215'. Slit 217 demonstrates a fourth type of width defect as it is wider than slit 215, i.e. 217' is greater than 215'.

It should be appreciated that the concepts of pitch, pitch defect, and width defect may be defined in numerous ways. For example, pitch might be calculated as the distance between the centers of two adjacent slits or between the centers of two adjacent ribbons. A pitch defect might be defined as a pitch which falls outside a predetermined range of pitches. Further, it should appreciated that any portion of an aperture grill may include one or more under-etch, over-etch, pitch, and width defects.

Although automatic visual inspection systems have been created to meet the inspection demands of a variety of specific manufacturing applications, the inspection of aperture grills has yet to be automated. A visual inspection system 18 is illustrated in FIG. 2. As shown therein, such a system 18 includes a transport mechanism 22, a scanner 20, a processor 19, a sorter 24, a "good" bin 21, and a "bad" bin 26.

In the system 18 of FIG. 2, the transport mechanism 22 conveys a series of objects 23 through the scanning field of scanner 20 to the sorter 24. Scanner 20 acquires a visual image of each object 23 and sends the image to the processor 19 to be analyzed. The processor 19 analyzes the visual image corresponding to each of the objects 23 and classifies the particular object 23 as either "good" or "bad." Accordingly, the processor 19 controls the operation of sorter 24, causing it to route each object 23 to either the "good" bin 21 or the "bad" bin 26.

To date, aperture grills have been considered unsuitable for automatic visual inspection due to the limited resolution of available imaging technology and the considerable expense of hardware capable of processing vast amounts of image data at assembly-line speeds. In developing an automatic visual inspection system, one problem encountered has been the provision of lighting sufficient to illuminate, for accurate visual inspection, a moving web of aperture grills. Variations in the velocity at which a web is propelled have been found to influence the intensity of the light which passes through the grills. Such variations in velocity may be caused by assembly-line stoppages, changes in the work pieces, the addition or removal of different types of processing or assembly steps for different products, or simply inconsistent motor operation. In an inspection system which acquires images of aperture grills by measuring the intensity of light passing through different areas of the grills, it is critical that velocity-induced effects on the intensity of light be accounted for or mitigated.

Further, in an inspection apparatus comprising multiple visual inspectors (e.g. cameras) in close proximity, it is possible that light which has been reflected, passed, or defracted by one portion of an aperture grill may contaminate images obtained of other portions of that or another grill. Consequently, careful positioning of light-emitting elements and suitable limitation of the beams of light produced thereby are needed. Additionally, the light-emitting elements may require special positioning to accommodate the effects of light diffraction in certain applications.

OBJECTS AND SUMMARY OF THE INVENTION

Therefore, an object of the present invention is to provide adaptive lighting control apparatus for illuminating a variable-speed web for inspection by an automatic visual inspection system in a manufacturing environment.

It is an additional object of the present invention to provide lighting control apparatus for illuminating a variable-speed web comprised of aperture grills having a plurality of slits with respective edges for inspection.

Another object of the present invention is to provide lighting control apparatus for illuminating a variable-speed web comprised of aperture grills for automatic visual measurement of the pitch of ribbons and slits of the aperture grills.

A further object of the present invention is to provide lighting control apparatus for illuminating a variable-speed web comprised of aperture grills for automatic visual measurement of the widths of ribbons and slits of the aperture grills.

A still further object of the present invention is to provide lighting control apparatus for varying the intensity of light emitted by one or more light-emitting elements which illuminate a variable-speed web comprised of aperture grills.

Yet another object of the present invention is to provide lighting control apparatus, for varying the voltages applied to one or more light-emitting elements which illuminate a variable-speed web comprised of aperture grills.

In accordance with an aspect of the present invention, a lighting control apparatus for illuminating a moving variable-speed web for inspection with a camera is provided. The apparatus is comprised of a detecting device for detecting and generating a signal representative of a plurality of positions of the web and a lighting device, aligned with the camera, for emitting a light to illuminate the web. The apparatus further includes a calculating device, coupled to the detecting device, for calculating the speed of the web. A control device, coupled to the calculating device and to the lighting device, controls the emission of light by the lighting device as an increasing function of the calculated speed.

In accordance with another aspect of the present invention, a lighting control apparatus for illuminating a variable-speed web for inspection with a first plurality of cameras and with a second plurality of cameras is provided. The apparatus is comprised of a detecting device for detecting and generating a signal representative of a plurality of positions of the web and a first plurality of lighting devices, aligned with the first plurality of cameras, for emitting light to illuminate the web. Also provided are a second plurality of lighting devices, aligned with the second plurality of cameras, for emitting light to illuminate the web. A calculating device, coupled to the detecting device, for calculating the speed of the web is provided, along with a control device, coupled to the calculating device and to the first and second pluralities of lighting devices, for controlling light emission of each of the first plurality of lighting means as an increasing function of the calculated speed and for controlling light emission of each of the second plurality of lighting means as yet another function of the calculated speed.

In each of the aforementioned aspects of the invention it should be noted that the object to be inspected could be an aperture grill having slits, a shadow mask having circular holes or rounded slots, or any other perforated device.

Other objects, features, and advantages according to the present invention will become apparent from the following detailed description of illustrated embodiments when read in conjunction with the accompanying drawings in which the same components are identified by the same reference numerals.

BRIEF DESCRIPTION OF THE DRAWINGS

FIG. 1A is a diagram of an aperture grill;

FIGS. 1B and 1C are diagrams of portions of the aperture grill of FIG. 1A;

FIG. 2 is a diagram of a general automatic visual inspection apparatus;

FIGS. 7A–7D are signal diagrams to which reference will be made in explaining the operation of the edge detection apparatus of FIG. 4;

FIG. 8 is a diagram of pixels representing edges of an aperture grill;

FIG. 11 is a graph of voltage versus web speed to which reference will be made in explaining the operation of the lighting control apparatuses of FIG. 9 and FIG. 10.

DETAILED DESCRIPTION OF THE PREFERRED EMBODIMENTS

Figure 1C:
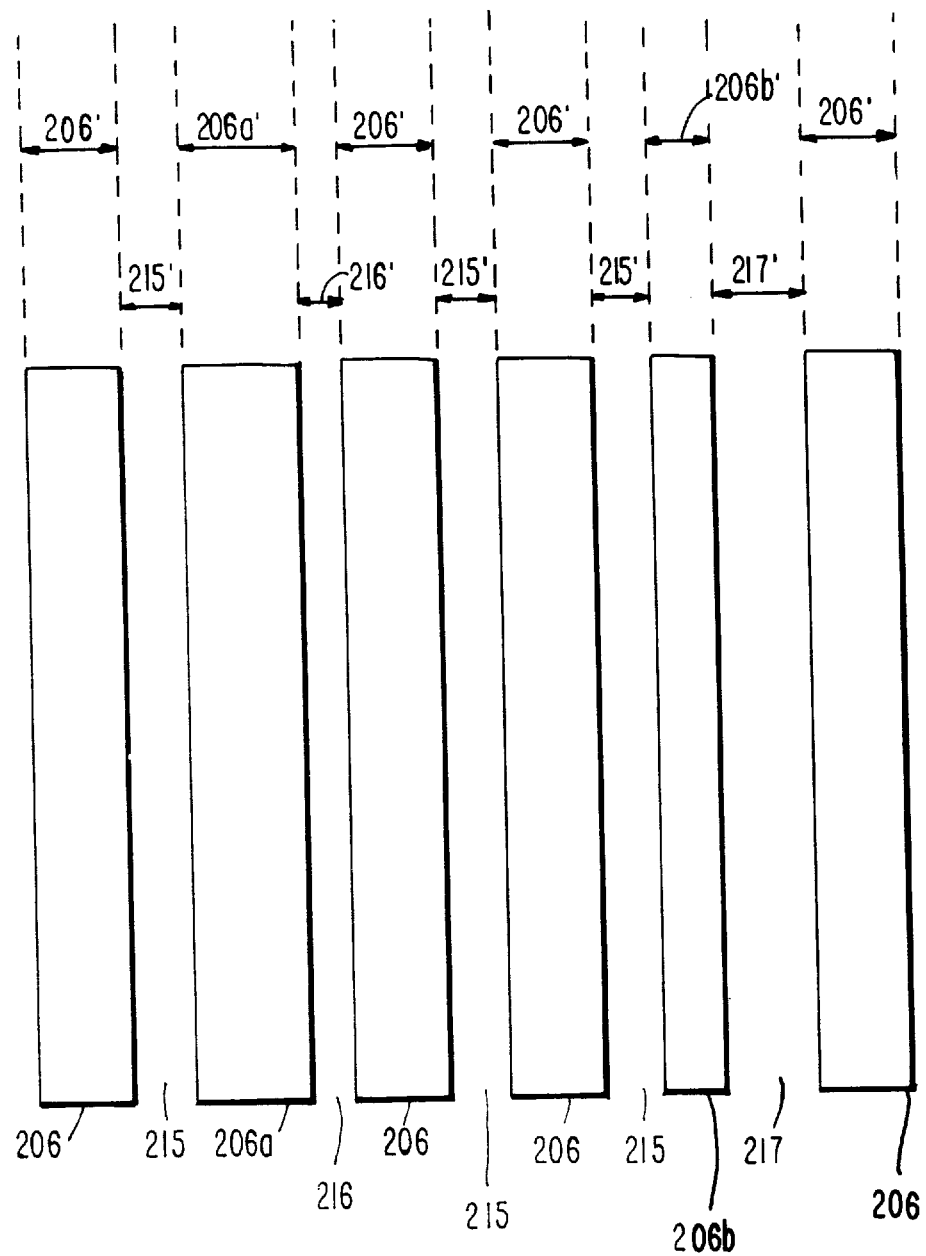
Figure 3:
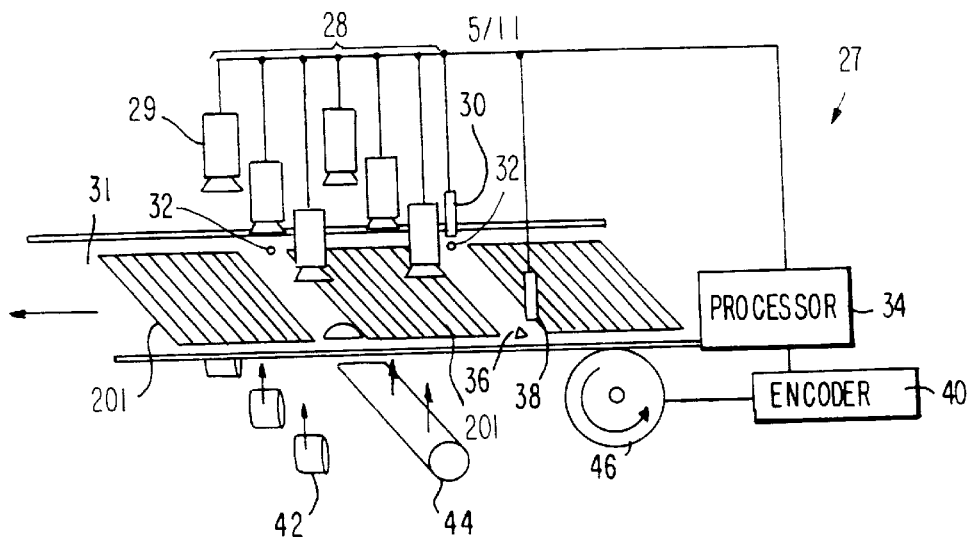
FIG. 3 is a schematic diagram of an automatic visual inspection apparatus incorporating a lighting control apparatus according to an embodiment of the present invention.

FIG. 3 illustrates automatic visual inspection apparatus 27 for inspecting an entire aperture grill. The apparatus 27 generally includes a camera array 28, a mask sensor 30, a processor 34, a cycle detector 38, an encoder 40, lighting devices 42 and 44, and a motor 46. Each aperture grill 201, hereinafter "grill", is situated on a web 31 and is separated from the adjacent grills by mask holes 32 in web 31. Further, groups of grills are delineated by cycle hole 36 in web 31. In the preferred embodiment, a single cycle of aperture grills consists of a group of twenty-seven grills.

Camera array 28 is comprised of one or more cameras 29 adapted to acquire images of an object as pixels of image data. Typically, each camera 29 is comprised of a plurality of light-sensitive sensors, each of which produces light intensity values as a function of the amount of incident light. A light intensity value, matched with the relative coordinates of the sensor, forms a pixel. Thus, the acquired image is represented by a plurality of pixels, each pixel having a light intensity value and identifying coordinates. Each camera 29 in the array 28 may be associated with a microprocessor system (such as a Motorola 68040 microprocessor-based system) and/or a dedicated image processor (such as a Datacube MAXTD) for immediate data processing of acquired image data.

Mask sensor 30 and cycle detector 38 are detection devices that sense the presence of markings on web 31. Mask hole 32 and cycle hole 36 are two such markings, preferably arranged at opposite ends of web 31 to avoid erroneous detections.

Processor 34 is connected to each camera 29 in camera array 28, mask sensor 30, cycle detector 38, encoder 40, and lighting devices 42 and 44. Processor 34 is a software-controlled microprocessor-based system (such as a Motorola 68040 microprocessor-based system) which receives input signals from camera array 28, mask sensor 30, cycle detector 38, and encoder 40. Based upon the input signals, processor 34 provides control signals to lighting devices 42 and 44 and to camera array 28. Through control signals, processor 34 coordinates the movement, lighting, and scanning of the aperture grills 201 to assure system-wide synchronization.

Also, processor 34 is coupled to and provides information signals to one or more peripheral devices (not shown). The peripheral devices may include data storage devices, performance monitoring devices, sorting devices, marking devices, etc. The information signals may detail the operating characteristics of the various components of the automatic visual inspection system 27 and may include real-time inspection information regarding the aperture grills 201.

Motor 46 is mechanically engaged with web 31, driving web 31 forward as indicated by the arrow in FIG. 3. As web 31 moves forward, it carries a plurality of aperture grills 201 through the scanning fields of camera array 28, mask sensor 30, and cycle detector 38. Processor 34 collects information relating to the position and speed of the web from mask sensor 30, cycle detector 38, and encoder 40 and determines the position and speed of the web and the beginning of a cycle of grills and/or the beginning of a single grill. Based upon the position and speed of the web, processor 34 calculates the appropriate light intensity level for each of lighting devices 42 and 44 and provides appropriate intensity signals to each.

Encoder 40 is a detection device for monitoring the operation of motor 46. As motor 46 turns, propelling web 31 forward, encoder 40 detects the change in position of the motor and generates a position signal representative thereof. For example, each increment of rotation of the motor may be represented by a single digital pulse.

As will be appreciated by one of ordinary skill, since the linear displacement of web 31 can be expressed as a function of the angular displacement of motor 46, the position and speed of the web, and the like, can be determined from the position signal. In a preferred embodiment, the encoder is configured to generate one digital pulse each time the motor rotates through an angle sufficient to drive the web a certain distance, for example 25, 50 or 100 microns. Encoder 40 supplies the position signal to processor 34 and/or to camera array 28 directly. Processor 34 is adapted to calculate from the position signal and other input data the position and speed of web 31, or the like, and generate appropriate control signals for supply to the camera array and the lighting devices. Alternatively, microprocessor systems associated, respectively, with each of the cameras in array 28 may perform such calculations and the like. Preferably, the position signal from encoder 40 is supplied directly to one or more cameras in camera array 28 to synchronize camera operation with movement of the aperture grills.

Each camera 29 in array 28 acquires image data representing a portion of an aperture grill 201 which has passed through its scanning field. Acquired image data is transmitted to processor 34 for processing and analysis. Optionally, acquired image data is pre-processed locally by individual microprocessor systems associated, respectively, with each camera 29 prior to being transmitted to processor 34. Processor 34 processes the image data and analyzes the processed data for indications of defective aperture grills in the manner to be described below. The location and type of each defect, along with other information regarding each aperture grill, may be stored or provided to peripheral devices.

Figure 4:
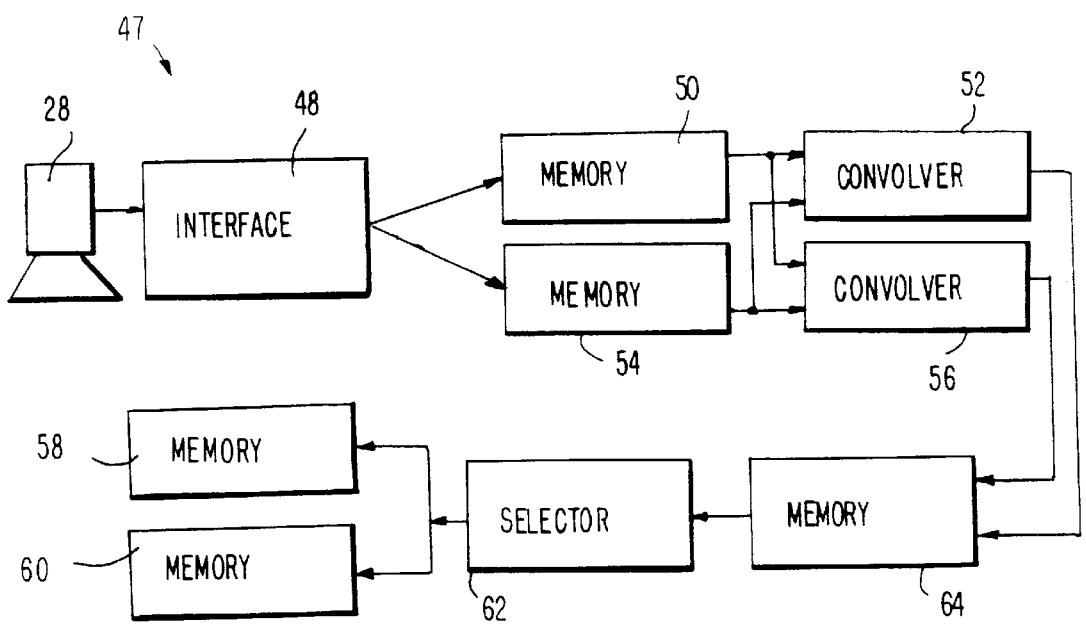
FIG. 4 is a block diagram of edge detection apparatus.

In one embodiment, camera 29 and processor 34 of FIG. 3 form an edge detection apparatus 47, as illustrated in detail in FIG. 4. The edge detection apparatus 47 is comprised of camera 29; interface 48; buffer memories 50 and 54; edge memories 58 and 60; and look-up table memory 64; convolvers 52 and 56; and selector 62. Edge detection apparatus 47 has a pipelined architecture, facilitating the storage, processing, and compression of large quantities of pixel data at assembly-line speeds. An automated visual inspection system incorporating this edge detection apparatus quickly and efficiently identifies the edge of an inspected object and thus alleviates the inspection bottleneck which has substantially limited prior art manufacturing efforts.

Camera 29 is a conventional scanning device, such as a Dalsa linescan camera that generates one line of image data formed of 2048 pixels. Preferably, lines of image data are acquired at approximately 100 micron intervals along each aperture grill. Each sensor of the Dalsa camera has an 8×8 micron resolution resulting in an overall scan width of 16.384 mm. The Dalsa camera acquires 1,650 lines per second to produce 3.379M pixels of information per second. Interface 48 is coupled to and receives lines of pixel data from camera 29 and is also connected to each of buffer memories 50 and 54 to selectively provide each buffer memory with such lines of pixel data. Buffer memories 50 and 54 serve as buffers to store and provide blocks of pixel data to convolvers 52 and 56.

In a preferred embodiment, interface 48 alternately provides a group of lines of pixel data to each of buffer memories 50 and 54. After receiving each group, the respective memory provides the received group to both of convolvers 52 and 56. Thus, buffer memories 50 and 54 operate to alternately store and read out pixel data and thereby serve as buffering storage for the acquired image. Alternatively, interface 48 and buffer memories 50, 54 could be replaced by a single memory unit capable of simultaneously reading and writing stored information.

Convolvers 52 and 56, also referred to as "neighborhood multiplier accumulators", are coupled to look-up table memory 64, and operate upon groups of pixels to produce a series of look-up table memory addresses. It is preferred that each of convolvers 52 and 56 operates upon 6×1 groups of pixel data to produce a look-up table address coordinate. Taken together, two look-up table address coordinates, one output from each convolver, form a look-up table memory address. Look-up table memory addresses, along with the location coordinates of each corresponding group of pixels, are provided to memory 64. The location coordinates serve to identify the location of the particular group of pixels in an acquired image.

Convolvers 52 and 56 each conduct a convolution operation upon a group of pixels. In a preferred convolution operation, the light intensity values of a group of pixels are multiplied by an array (or kernel) of values having dimensions similar to that of the group The results of these multiplications are summed to produce a single convolution result. The convolution result may serve as a look-up table memory address directly or first be subjected to further processing.

Each of convolvers 52 and 56 is preferably comprised of a series of multipliers and adders. Alternatively, a convolver is comprised of one or more arithmetic units or processors for achieving the convolution result.

Look-up table memory 64 is pre-stored with values and is coupled to selector 62. Look-up table memory 64 functions as a look-up table, accessing one or more stored values in response to each address provided by convolvers 52 and 56. Accessed values, along with location coordinates for each corresponding group of pixels, are output to selector 62.

Selector 62 selects local minima from among the accessed values received from the look-up table memory 64. Selector 62 is coupled to edge memories 58 and 60 and provides one memory with selected local minima and the other with location coordinates for each corresponding group of pixels. Preferably, selector 62 is arranged as a pipelined series of memories and arithmetic logic units. Edge memories 58 and 60 store the data provided by selector 62.

In operation, camera 29 scans an aperture grill having a series of alternating ribbons and slits in a direction substantially perpendicular to the orientation of the ribbons and slits. Light shining through the bottom surface of the aperture grill creates an image projected to the camera as alternating bands of light, dark, and shades of grey. Further operation of edge detection apparatus 47 will be explained in conjunction with FIGS. 5, 6, 7A–D, and 8.

Figure 5:
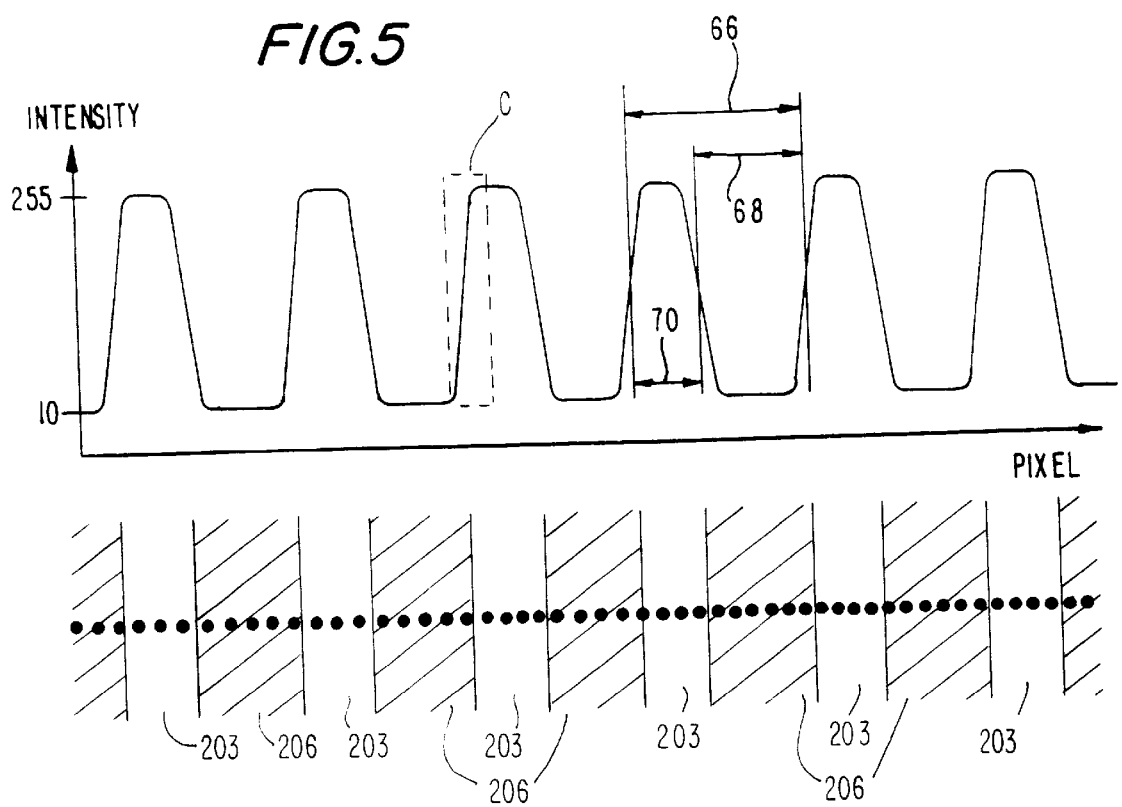
FIG. 5 is a graph of pixel intensities along with a diagram of an aperture grill to which reference will be made in explaining the generation of an image signal.

The graph of FIG. 5 depicts the light intensity values of a line of pixels which represent a portion of an aperture grill. Below the pixel versus intensity graph is the corresponding cross section of the aperture grill upon which the discrete areas imaged by the pixels have been superimposed. The light intensity value of each pixel can range between 0, corresponding to absolute darkness, and 255, corresponding to bright light, varying smoothly between the two extremes. Slits in the aperture grill are represented by pixels having large intensity values (255) while ribbons are represented by pixels having small intensity values (10). As illustrated, the slits 203 appear to the camera as areas of high light intensity, and thus pixels imaging slit areas have high light intensity values. In contrast, the ribbons 206 appear to the camera as areas of low light intensity, and thus pixels imaging ribbon areas have low light intensity values.

The shared edge of a slit and an adjacent ribbon is estimated as the point on the curve of FIG. 5 which has a light intensity value approximately halfway between the two extreme intensity values. In this example, the halfway point has an intensity value on the order of 127.5 (=0.5×255). The location of an edge is roughly approximated by the coordinates of the pixel having an intensity value nearest to the halfway point. A more accurate estimate is obtained by calculating the distance between a nearby pixel and the halfway point.

A pitch 66 is calculated as the distance between two halfway points which approximate the locations of two adjacent corresponding edges. A ribbon width 68 is calculated as the distance between two halfway points which approximate the locations of the two edges of a ribbon. Further, a slit width 70 is calculated as the distance between two halfway points which approximate the locations of two edges of a slit.

Camera 29 provides a plurality of lines of pixels to interface 48 which selectively distributes the pixels to each of buffer memories 50 and 54. In turn, buffer memories 50 and 54 provide pixels to each of convolvers 52 and 56. Each convolver 52 and 56 performs a convolution operation on a group of pixels and together provide a look-up table memory address to access a memory location in look-up table memory 64. The convolution operation and its interrelationship with the values stored in look-up table memory 64 will be explained in conjunction with FIG. 6.

Figure 6:
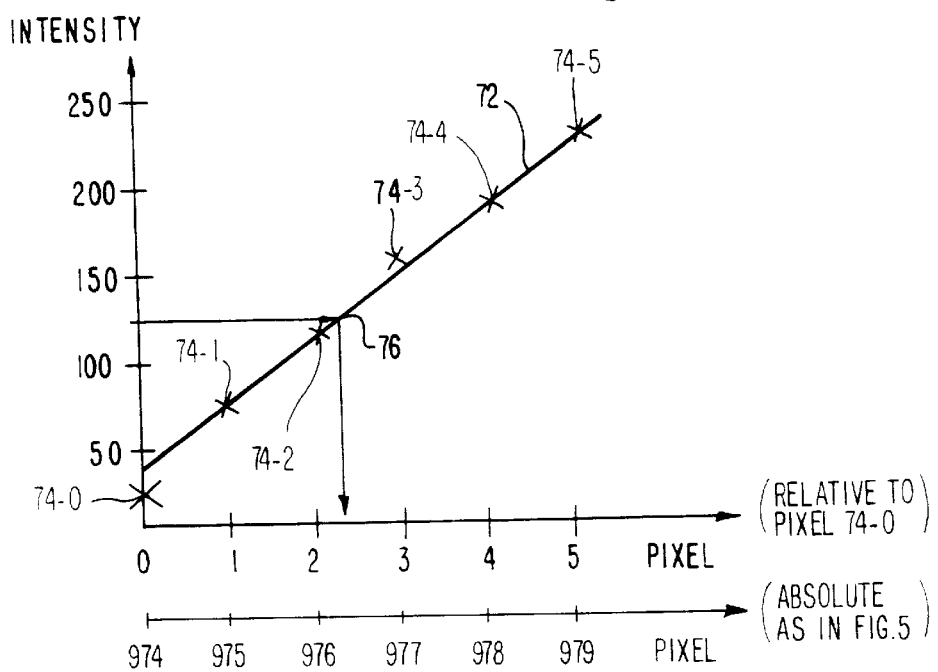
FIG. 6 is a graph of pixel intensities to which reference will be made in explaining the derivation of a linear relationship from a set of light intensity values.

FIG. 6 illustrates a portion C of the curve in FIG. 5 comprised of six individual pixels 74-0, 74-1, 74-2, 74-3, 74-4, and 74-5, collectively "pixels 74." The graph of FIG. 6 includes two horizontal axes: an upper axis indicating pixel position relative to pixel 74-0 and a lower axis indicating actual pixels corresponding to those of FIG. 5. Each of pixels 74 is produced by one of a series of adjacent light-sensitive sensors in camera 29 during a single scan by the camera. Pixels 74 have consecutively increasing intensity values which is characteristic of a ribbon-slit edge. Conversely, consecutive pixels having decreasing intensity values is characteristic of a slit-ribbon edge. The group of pixels 74 is approximated by line 72 which is obtained by performing a linear regression operation on the six pixels 74. The line 72, in particular the segment of line 72 extending from pixel 74-0 to pixel 74-5, thus approximately describes the change in light intensity that occurs over the area represented by the six pixels 74.

The six pixels 74 exhibit a range of light intensity values from a low of about 20 to a high of about 225. Since a light intensity value of a halfway point, for example 127.5, must exist between the two extreme intensity values of the six pixels 74, it is surmised that an edge is spanned by the six pixels 74. An approximate location of the halfway point is calculated simply by substituting the value 127.5 into the linear equation which defines line 72 to produce the corresponding pixel coordinate. The point on line 72 having an intensity value of 127.5 is identified by reference numeral 76, and has a pixel coordinate of 2.3, relative to pixel 74-0.

Once the pixel coordinate of point 76 is calculated, the distance (in pixel units) between point 76 and the pixels can be determined. For example, point 76 is a distance of 1.3 pixels from pixel 74-1, 0.3 pixels from pixel 74-2, 0.7 pixels from pixel 74-3, and 1.7 pixels from pixel 74-4.

In a preferred embodiment, line 72 is defined by the equation I=mP+b, where I is light intensity, m is the slope, P is pixel coordinate relative to pixel 74-0, and b is the offset from zero intensity. The six points 74 are expressed in (pixel coordinate, intensity) form as $(0, I_0)$, $(1, I_1)$, $(2, I_2)$, $(3, I_3)$, $(4, I_4)$, and $(5, I_5)$. By substituting each of points 74 into the general equation for a line, such as line 72, a set of six equations is obtained (not shown here). By simultaneously solving these six equations, six specific coefficients are derived, from which expressions for m and b are obtained in terms of the intensity values of the six pixels 74. Specifically, slope $m=-0.1429I_0-0.0857I_1-0.0286I_2+0.0286I_3+0.0857I_4+0.1429I_5$ and offset $b=0.5238I_0+0.3810I_1+0.2381I_2+0.0952I_3-0.0476I_4-0.1905I_5$. Assuming a left-to-right scan, the slope m will have a positive value if the six pixels 74 span a ribbon-slit edge and a negative value if the six pixels 74 span a slit-ribbon edge.

The convolution operation of convolver 52 is preferably a calculation of the slope m as described above. In a preferred embodiment, convolver 52 is preset with the six coefficients, −0.1429, −0.0857, −0.0286, 0.0286, 0.0857, and 0.1429, which are needed to calculate the value of the slope m of a group of six pixels. Presented with six consecutive pixels 74 by one of buffer memories 50 and 54, convolver 52 calculates the corresponding value of slope m. Following the same procedure, convolver 56 calculates the value of offset b corresponding to the six pixels 74. In this manner, each group of six pixels 74 is approximated by a line defined by a particular combination of slope m and offset b values.

The two values m and b, corresponding to a particular group of six pixels 74, are provided by convolvers 52 and 56, respectively, to look-up table memory 64. Additionally, location coordinates for a reference pixel from the particular group of six pixels 74 are provided. Preferably, the first pixel (e.g. 74-0) of a group of six pixels 74, is utilized as the reference pixel. The location coordinates define the location of the reference pixel, and thus the group of pixels, in an acquired image. By repeating the above-described procedure, convolvers 52 and 56 process lines of pixel data supplied by buffer memories 50 and 54 in groups of six pixels at a time.

In a preferred embodiment, a first group of six pixels is defined from a line of pixels as the first six adjacent pixels starting at one end of the line of pixels. Subsequent groups of six pixels are defined as five adjacent pixels of the preceding group plus the next adjacent pixel. Thus, each group of pixels is offset by one pixel from its two neighboring groups.

As an example, a line defined by eight adjacent pixels (pixels 1–8) would include three consecutive groups of six pixels (pixels 1–6, pixels 2–7, pixels 3–8). As a result, each aperture grill edge is typically spanned by five consecutive groups of six pixels. In the case where a pixel is exactly aligned with a particular edge, six consecutive groups of six pixels span the edge. As an example, by extrapolating the absolute pixel scale of FIG. 6 in both directions, it can be seen that the halfway point 76 is spanned by five consecutive groups of pixels: pixels 972–977, pixels 973–978, pixels 974–979, pixels 975–980, and pixels 976–981. However, if halfway point 76 was exactly aligned with pixel 976, then it would be spanned by six consecutive groups of pixels: pixels 971–976, pixels 972–977, pixels 973–978, pixels 974–979, pixels 975–980, and pixels 976–981.

Given the known resolution of the values output by convolvers 52 and 56, the finite range of intensity values, and the fixed number of pixels approximated by each line, the different possible combinations of slope m and offset b values may be readily anticipated. From each anticipated combination of slope m and offset b values, the pixel distance between a reference pixel and the halfway point, located on the line defined by the particular combination of slope m and offset b values, can be calculated in units of pixels. This pixel distance is referred to as an edge offset value and represents the distance between the reference pixel and an edge.

If the reference pixel is defined as the first pixel from each group of pixels, then the edge offset values for each group spanning an edge range from zero to the total number (N) of pixels in the group minus one. An edge offset value of zero indicates that the first pixel is aligned with the edge while a value of N−1 indicates that the last pixel in the group is aligned with the edge. Edge offset values between zero and N−1 indicate that the edge lies between the first and last pixels at a distance equal to the edge offset value (in pixels units) from the first pixel. Each succeeding consecutive group of pixels spanning the same edge will necessarily have an edge offset value that is one pixel less than its immediately preceding neighboring group.

Look-up table memory 64 is pre-stored with edge offset values corresponding to possible combinations of slope m and offset b values. Since the maximum possible edge offset value is equal to the total number of pixels in the group minus one, the size of look-up table memory 64 is minimized. Each pair of slope m and offset b values serve as a look-up table memory address for look-up table memory 64. Upon receiving a look-up table memory address, look-up table memory 64 provides the corresponding pre-stored edge offset value to selector 62.

Alternatively, look-up table memory 64 may be pre-stored with edge offset values corresponding to a subset of the possible combinations of slope m and offset b values. When look-up table memory 64 receives addresses derived from combinations of slope m and offset b values outside this subset, it provides an out-of-range value to selector 62. In the preferred embodiment, this out-of-range value equals 255.

For each group of six pixels processed by convolvers 52 and 56, look-up table memory 64 supplies to selector 62 the location coordinates of the reference pixel in the group and either an edge offset value or an out-of-range value. If an out-of-range value is received, that value and its corresponding coordinates are discarded. From the set of five or six consecutive groups of pixels which span a particular edge, selector 62 selects the group having the minimum edge offset value. The edge offset value of the selected group is provided to edge memory 58 and its location coordinates are provided to edge memory 60.

FIGS. 7A–D are waveform diagrams which are helpful in explaining the preferred operation of selector 62. In FIG. 7A, as in FIG. 5, the vertical axis represents intensity and the horizontal axis represents pixels. FIG. 7A presents a graphical representation of a single slit in an aperture grill. The left and right edges of the slit are indicated by "X" marks 76 and 77, respectively. As the slit is scanned from left to right, pixels 82 and 86 are the pixels closest to marks 76 and 77 respectively. It should also be noted that groupings of six adjacent pixels, taken from left to right, that begin with any of points 78 fail to span either of edges 76 and 77.

In FIGS. 7B and 7C, the vertical axis represents edge offset values and the horizontal axis represents pixels; however, the figures are not to scale. FIG. 7B presents a graphical representation of the edge offset values read from look-up table memory 64 corresponding to the pixels of FIG. 7A in which the left-most (first) pixel of each group is the reference pixel for that group. Points 78 all have the same intensity, an out-of-range value equal to 255. Groupings of six adjacent pixels, taken from left to right, that begin with any of points 80, 82, 84, or 86 span one of edges 76 and 77. Each of points 80, 82, 84, and 86 is labelled with its respective edge offset value. As illustrated, points 82 and 86 are 0.5 pixel units away from edges 76 and 77, respectively.

FIGS. 7C and 7D illustrate a preferred method of selecting pixels having minimum edge offset values. FIG. 7C is a copy of FIG. 7B shifted to the left by one pixel. By appropriately buffering the stream of edge offset values supplied thereto, selector 62 shifts the input stream to the left by one pixel and subtracts the shifted input stream from the unshifted input stream. In effect, the values of FIG. 7C are subtracted from the values of FIG. 7B. The negative results of this subtraction correspond to pixels having a minimum edge offset value.

The result of this subtraction operation is illustrated in FIG. 7D, wherein negative results are mapped to binary 1 and all others to binary 0. Accordingly, points 92, having a value of binary 0, correspond to the aggregate of points 78, 80, and 84. Points 88 and 90, having values of binary 1, correspond to points 82 and 86, respectively. Thus, the point closest to each edge (e.g., points 82 and 86), when approaching from the left, is identified and selected (as indicated by points 88 and 90).

Selector 62 repeats the above-described selection process for each set of five or six groups of pixels spanning each edge of the aperture grill. Edge memories 58 and 60 store the offset value and location coordinates, respectively, of each of the selected pixel groups. In the preferred embodiment, as mentioned above, the location coordinates identify the first pixel of a group The selected and stored location coordinates and offset values thus describe the location of each edge of the aperture grill with sub-pixel accuracy. The location defined by a particular set of location coordinates and offset values will be referred to hereinafter as an edge point.

FIG. 8 provides a graphical representation of edge location information stored in edge memories 58 and 60. Each edge of the aperture grill appears as a substantially straight line of edge points. Ribbon 94 and adjacent slit 96 are defined, respectively, by pairs of edge points which appear as two substantially straight lines of edge points. For example, ribbon 94 is defined by edge points 93 and 95. The lines of edge points appear slanted because the aperture grill moves between consecutive scans by the camera.

The above description of edge detection apparatus 47 is intended to illustrate an application suitable for use in conjunction with the present invention and not as a limit thereon. Each element of apparatus 47 is readily adaptable to process pixel groups and pixel data organized in a form other than 6×1 blocks. The interpolation of a more precise estimate of the location of an edge can be achieved by a number of straightforward variations on the linear regression operation described. For example, polynomial, sinusoidal, and other well-known techniques of curve-fitting may also be implemented with a pipelined arrangement of convolvers and memories to estimate the location of an edge. Variations on these techniques are contemplated to process lines of pixel data scanned oblique to the edge of an aperture grill. More precise interpolations are expected to be obtained through two-dimensional convolution operations which utilize a series of convolver and memory elements. Further, even greater precision may be obtained by repeating the scanning and interpolating processes for each edge and averaging together the interpolated results. This last method has the added benefit of removing errors introduced by irregular movements of the scanned aperture grill on an assembly line.

Figure 9:
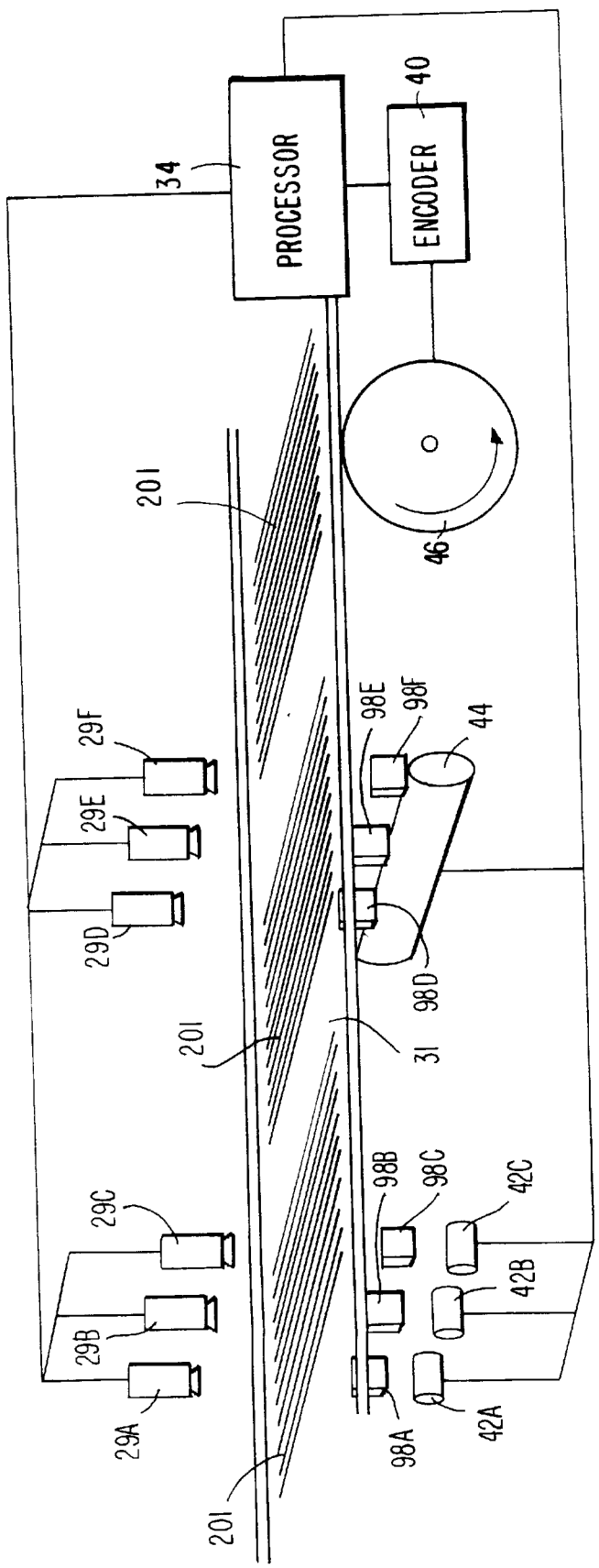
FIG. 9 is a schematic diagram of an automatic visual inspection apparatus incorporating a lighting control apparatus according to another embodiment of the present invention.

FIG. 9 presents a schematic diagram of lighting control apparatus according to an embodiment of the present invention incorporated into an automatic visual inspection apparatus. The apparatus is comprised of cameras 29A–F, processor 34, encoder 40, motor 46, lighting devices 42A–C and 44, and regulators 98A–F. Also illustrated in FIG. 9 are web 31 and aperture grills 201. Motor 46, encoder 40, web 31, and aperture grills 201 have been described in sufficient detail in the preceding, and therefore, further discussion of these elements will be omitted. The following will include further description of additional aspects of cameras 29A–F and lighting devices 42A–C and 44 and of the operation of processor 34.

In a preferred embodiment, cameras 29A–C are configured to scan the aperture grills in a direction substantially perpendicular to the orientation of the ribbons of the grills. As described in the preceding, such cameras may be employed to determine the positions of the edges and the distances therebetween. In contrast, cameras 29D–F are configured to scan the aperture grills in a direction substantially parallel to the orientation of the ribbons of the grills. Such cameras may be employed to detect under-etch and over-etch defects in the tapes.

Lighting devices 42A–42C and 44 are conventional-type light-emitting elements suitable for use with optical inspection devices, such as video cameras. Preferably, the lighting devices are incandescent lamps, comprising Halogen bulb light sources, which are controlled by varying the input voltage applied to the device. Variation of the input voltage to such a lighting device will vary the intensity of the light output by the device. Each of lighting devices 42A–C and 44 is coupled to processor 34 which controls the intensity of the light emitted therefrom, preferably by controlling the voltage input thereto.

Lighting devices 42A–C and 44 have been described herein as four separate devices to facilitate explanation of the present invention and such an arrangement should not be considered a limitation on the present invention. It is well within the ordinary skill in the art to combine or subdivide like light sources for use in the apparatus of the present invention. Additionally, it is contemplated that other conventional means may be advantageously implemented according to the present invention to control the intensity of the light emitted by such light sources.

As illustrated, it is preferred that lighting devices 42A–42C and 44 are individually-controlled halogen bulbs, wherein the bulbs of devices 42A–42C are relatively shorter than the bulb of device 44. Further, it is preferred that the bulb of device 44 is arranged parallel to the ribbons of the aperture grills in alignment with cameras 29D–F while the bulbs of devices 42A–42C are arranged perpendicular (in the plane of the web) to the ribbons of the aperture grills in alignment with cameras 29A–29C, respectively. This particular configuration of lighting devices has been found to optimize the quality of the images acquired by the cameras. Specifically, image quality is maximized where the light device is arranged parallel to the scanning direction of the camera.

Interposed between each of lighting devices 42A–C and web 31 is one of regulators 98A–C, aligned with the respective lighting device. Similarly, regulators 98D–F are interposed between lighting device 44 and web 31 and aligned with device 44. Regulators 98A–F may comprise any combination of a variety of light-influencing objects or apparatuses, such as a lens array, a fiber optic bundle, an iris diaphragm, a reflector, a polarizer, and the like, and each of the regulators need not be the same. The regulators serve to focus or otherwise influence light supplied by the lighting devices to sufficiently light the aperture grills. Additionally, the regulators may serve to direct light towards only select cameras and thereby prevent contamination of images acquired by other cameras by straying light. Optionally, the regulators may be coupled to and controlled by processor 34 or omitted entirely.

Figure 10:
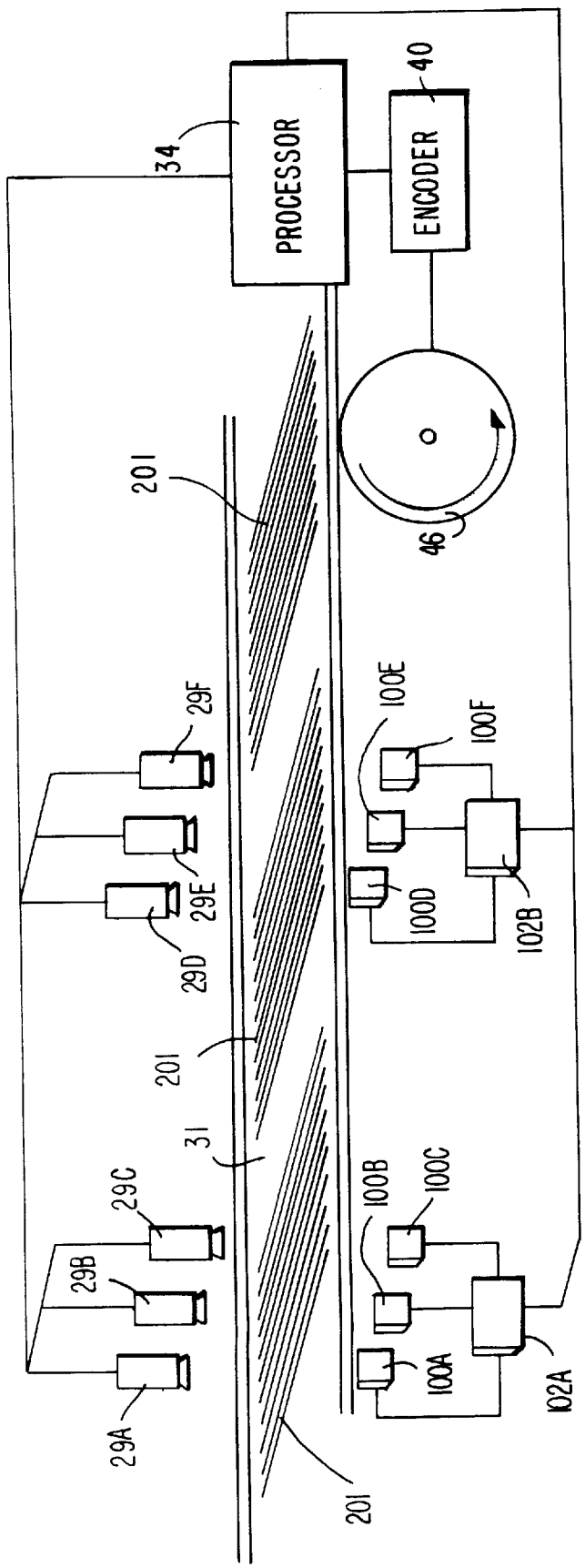
FIG. 10 is a schematic diagram of an automatic visual inspection apparatus incorporating a lighting control apparatus according to another embodiment of the present invention.

FIG. 10 illustrates another embodiment of the lighting control apparatus according to the present invention. This embodiment is the same as the apparatus of FIG. 9, except that regulators 98A–F are omitted and lighting devices 42A–C and 44 are replaced with light sources 102A and 102B and fiber optic terminations 100A–F. Light source 102A is coupled to fiber optic terminations 100A–C and light source 102B is coupled to fiber optic terminations 100D–F. These elements are coupled with fiber optic cables which carry light between the light sources and the terminations. Each termination directs the transmitted light through the web of aperture grills towards one or more of cameras 29A–F. Preferably, terminations 100A–F are aligned with cameras 29A–F, respectively.

Each of light sources 102A and 102B is coupled to processor 34 and receives a control signal therefrom. In response to the control signals, the light sources supply a certain amount of light through the fiber optic cables to fiber optic terminations 100A–C and 100D–F, respectively.

The operation of the lighting control apparatuses of FIGS. 9 and 10 will be described in the following with reference to FIG. 11. Encoder 40, coupled to motor 46 and processor 34, detects the motion of motor 46 and supplies a position signal indicative of such motion to processor 34. Processor 34 processes the position signal to calculate the speed at which web 31 is travelling by performing a derivative calculation upon the position signal, or some similar calculation. As a function of the speed of the web, processor 34 determines the proper voltage to be applied to each of the lighting devices. It has been found that, in general, the voltage applied to the devices should be increased as the speed of the web increases to maintain the quality of the images acquired.

For incandescent devices, the relationship between input voltage and output light intensity is generally nonlinear. Bearing this in mind, it was empirically determined that the dc voltage applied to the various lighting devices should be governed according to the relationships illustrated in FIG. 11.

In FIG. 11, the vertical axis represents the voltage output by processor 34 to a particular lighting device and the horizontal axis represents the speed of the web in units of meters-per-minute. For point of reference, application of zero voltage to a lighting device results in zero light output while application of five (5) volts results in a saturated output of light. Two increasing piecewise linear continuous curves are depicted, representing the two empirically-derived increasing piecewise linear continuous voltage versus speed functions, corresponding to the lighting requirements of two different types of camera configurations. As will be apparent to one of ordinary skill in the art, according to the illustrated functions, the voltage applied to a lighting device should be increased or controlled to be substantially constant as the speed of the web increases. Conversely, the voltage applied should be decreased or controlled to be substantially constant as the speed of the web decreases.

The "etch" curve corresponds to cameras 29D–F, which scan in a direction parallel to the ribbons of the aperture grill, and is therefore used to control lighting devices 42A–C. The "measure" curve corresponds to cameras 29A–C, which scan in a direction perpendicular to the ribbons of the aperture grill, and is therefore used to control lighting device 44. Processor 34 preferably includes a look-up table of values corresponding to the illustrated curves indexed according to speed values. In particular, the table includes parameters defining each line segment of both of the curves. Such a look-up table may be implemented with a memory device or the like. Alternatively, the curves may be expressed mathematically and stored as equations.

Processor 34 calculates the current speed of the web and the average speed of the web from the last five (5) speed calculations. If the current speed varies from this average speed by more than a predetermined amount, preferably one (1) percent, then the current speed value is employed to index into the table to access parameters of the corresponding line segment. As a function of the accessed parameters, processor 34 calculates the corresponding voltage to be applied to each of lighting devices 42A–C and 44 or generates a corresponding control signal for light sources 102A and 102B. If the current speed varies from the average speed by less than the predetermined amount, then processor 34 controls each of the lighting devices or light sources to maintain its current level of output. In this manner, abrupt changes in the intensity and/or wavelength of the light which illuminates the web may be avoided.

As will be appreciated by one of ordinary skill in the art, the present invention is operable to inspect any type of perforated object both in whole and in part. Light passing through or reflecting off of the object to be inspected results in an image that is detected by the imaging device. In accordance with the techniques described herein or obvious modifications thereof or with known techniques, the detected image is processed to detect and classify defects in the object. Adaptation of the described embodiments to accommodate specific object configurations, specific processing criteria, or specific defect criteria clearly fall within the scope of the appended claims as such adaptation is obvious, in view of the present disclosure, to one of ordinary skill. Thus, it must be understood that the configuration of the object to be inspected by the apparatus of the present invention is not limited to the illustrative examples described herein.

Although illustrative embodiments of the present invention and modifications thereof have been described in detail herein, it is to be understood that this invention is not limited to these precise embodiments and modifications, and that other modifications and variations may be affected therein by one skilled in the art without departing from the scope and spirit of the invention as defined by the appended claims.

What is claimed is:

1. A lighting control apparatus for illuminating a moving variable-speed web for inspection with a first plurality of cameras and with a second plurality of cameras comprising:

detecting means, coupled to said web, for detecting a plurality of positions of said web as said web moves and for generating a signal representing said positions;

a first plurality of lighting means for emitting light to illuminate said web for inspection with said first plurality of cameras;

a second plurality of lighting means for emitting light to illuminate said web for inspection with said second plurality of cameras;

calculating means, coupled to said detecting means and responsive to said signal, for calculating a speed of said web; and control means, coupled to said calculating means and to the first and second pluralities of lighting means, for controlling said first plurality of lighting means to emit said light with an intensity that varies as an increasing function of said speed and for controlling said second plurality of lighting means to emit said light with an intensity that varies as another increasing function of said speed.

2. Apparatus according to claim 1 further comprising drive means, coupled to said detecting means, for driving said web in a direction.

3. Apparatus according to claim 2, wherein said drive means comprises a rotating motor and wherein said detecting means comprises encoder means for encoding rotation of said motor.

4. Apparatus according to claim 1, wherein said first plurality of lighting means and said second plurality of lighting means comprise a plurality of incandescent light sources.

5. Apparatus according to claim 4, wherein aid plurality of incandescent light sources comprise a plurality of halogen bulbs.

6. Apparatus according to claim 1, wherein said first plurality of lighting means and said second plurality of lighting means comprise a plurality of fiber optic devices which emit said light from fiber optic cables.

7. Apparatus according to claim 1, wherein said web includes a plurality of aperture grills having a plurality of ribbons and wherein said first plurality of lighting means are aligned such that said light is emitted parallel to said ribbons.

8. Apparatus according to claim 7, wherein said second plurality of lighting means are aligned such that said light is emitted perpendicular to said ribbons.

9. Apparatus according to claim 1, wherein the increasing functions are continuous functions.

10. Apparatus according to claim 9, wherein the increasing functions are piecewise linear.

11. Apparatus according to claim 1, wherein said control means controls said first plurality of lighting means by varying a voltage supplied to each of said first plurality of lighting means such that the intensity of said light emitted by said first plurality of lighting means is an increasing function of said speed.

12. Apparatus according to claim 1, wherein said control means controls said second plurality of lighting means by varying a voltage supplied to each of said second plurality of lighting means such that the intensity of said light emitted by said second plurality of lighting means is an increasing function of said speed.

13. Apparatus according to claim 1, wherein said control means controls an intensity of the light emitted by said first plurality of lighting means.

14. Apparatus according to claim 1, wherein said control means controls an intensity of the light emitted by said second plurality of lighting means.

15. Apparatus according to claim 1 further comprising first regulating means, interposed between said web and said first plurality of lighting means, for controlling the light emitted by said first plurality of lighting means such that said light emitted by said first plurality of lighting means is adequate to illuminate said web for inspection.

16. Apparatus according to claim 1 further comprising second regulating means, interposed between said web and said second plurality of lighting means, for controlling the light emitted by said second plurality of lighting means such that said light emitted by said first plurality of lighting means is adequate to illuminate said web for inspection.

* * * * *